(12) United States Patent
Doss et al.

(10) Patent No.: US 8,821,571 B2
(45) Date of Patent: Sep. 2, 2014

(54) COMPENSATORY CONTAINER

(75) Inventors: Mirko Doss, Frankfurt am Main (DE); Martin Baecke, Dessau-Roβlau (DE)

(73) Assignee: E.S. BIO-TECH Limited, Limassol (CY)

( * ) Notice: Subject to any disclaimer, the term of this patent is extended or adjusted under 35 U.S.C. 154(b) by 33 days.

(21) Appl. No.: 13/600,573

(22) Filed: Aug. 31, 2012

(65) Prior Publication Data

US 2013/0079874 A1    Mar. 28, 2013

(30) Foreign Application Priority Data

Sep. 27, 2011    (DE) .......................... 10 2011 053 988

(51) Int. Cl.
*A61M 1/10*    (2006.01)
*A61N 1/362*    (2006.01)
*A61N 5/00*    (2006.01)

(52) U.S. Cl.
USPC ................................ 623/3.16; 600/16; 604/8

(58) Field of Classification Search
USPC ........... 623/3.1, 3.16, 3.17; 600/16–18; 604/8
See application file for complete search history.

(56) References Cited

U.S. PATENT DOCUMENTS

| 4,938,766 A * | 7/1990 | Jarvik | 623/3.17 |
| 2010/0204539 A1 | 8/2010 | Tansley | |

FOREIGN PATENT DOCUMENTS

| DE | 696 22 757 | 3/2003 |
| DE | 10 2004 018 255 | 11/2005 |
| DE | 10 2005 058 409 | 6/2007 |
| EP | 2 319 454 | 5/2011 |
| WO | WO 89/01765 | 3/1989 |
| WO | WO 97/26929 | 7/1997 |

* cited by examiner

*Primary Examiner* — Bruce E Snow
(74) *Attorney, Agent, or Firm* — Jenkins, Wilson, Taylor & Hunt, P.A.

(57) ABSTRACT

The invention concerns compensatory container (1) to influence blood pressure, comprising volume chamber (2) with connectors (3) for connecting volume chamber (2) to a natural cardiovascular system, and in which a change in pressure in the cardiovascular system may effect a change in volume of volume chamber (2), as well as means of adjustment which limit the change in volume of volume chamber (2) in a lower pressure region below a pressure threshold of at least 100 mmHg to a maximum of 10 cm$^3$, and which, in an upper pressure region between the pressure threshold and 150 mmHg, effect a change in volume of volume chamber (2) of not less than 10 cm$^3$, whereby the means of adjustment comprise frame (4) and at least one flexible body (5) working in conjunction with such frame. Frame (4) and flexible body (5) are located outside volume chamber (2), with frame (4) having two front parts (6) and at least three support rods (7) connecting two front parts (6), between which is situated the at least one flexible body (5).

12 Claims, 2 Drawing Sheets

COMPENSATORY CONTAINER

CROSS-REFERENCE TO RELATED APPLICATION

Figure 1:
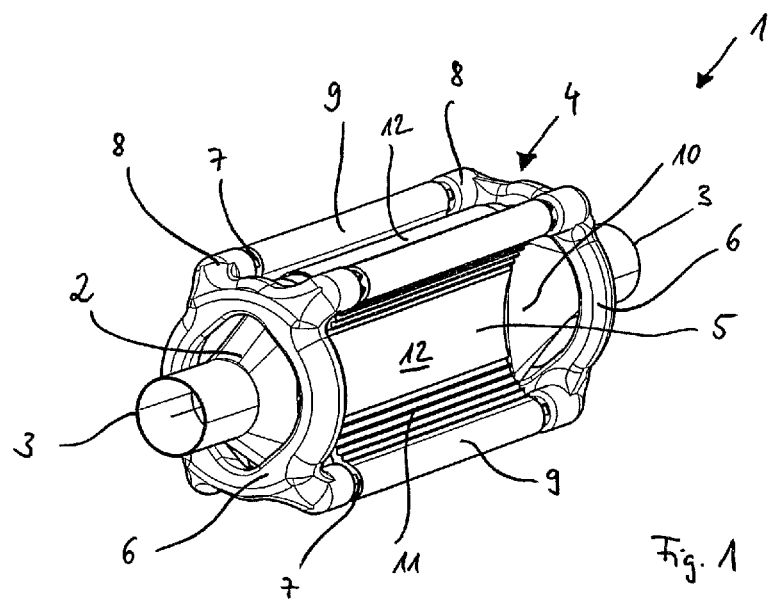

This application claims priority to German Patent Application No. 10 2011 053 988.3 filed on Sep. 27, 2011, the entire content of which is incorporated by reference herein.

DESCRIPTION

The present invention concerns a compensatory container for adjusting blood pressure. It consists of a volume chamber with connecting devices for attaching the volume chamber to a natural cardiovascular system, in which a pressure change in the cardiovascular system can effect a change in volume of the volume chamber. It also comprises means of adjustment, which limit the change in volume of the volume chamber in a lower pressure range below a pressure threshold of at least 100 mmHg to a maximum of 10 $cm^3$, and which effect a change in the volume of the volume chamber in an upper pressure range between the pressure threshold and 150 mmHg of at least 10 $cm^3$.

The term arterial hypertension, or high blood pressure, refers to a syndrome in which the blood pressure of the arterial vasculature is chronically elevated. According to the definition of the World Health Organization, sustained systolic blood pressure of more than 140 mmHg and diastolic blood pressure of over 90 mmHg is considered high blood pressure. Blood pressure is particularly prevalent in the western industrialized countries. Causes of the condition include, for example, genetic predisposition, the effects of medications, stimulants and drugs, as well as other health conditions. Sustained high blood pressure often leads to secondary damage, such as heart attacks and strokes.

The treatment of high blood pressure currently typically involves medication in conjunction with a lifestyle change. The success of both forms of therapy, however, is highly contingent on the patient's cooperation and readiness for such change. Older people often find it very difficult to change their lifestyle and to take their medication regularly. In addition, taking medications on a regular basis is often considered annoying and restrictive, and can represent a strain on other organs of the human body. Intolerance of medication has also been observed.

Attempts have accordingly already been made to provide devices that can affect blood pressure, and in particular that make it possible to treat high blood pressure, ideally with the need for medications.

Already known from DE 10 2005 058 409 A1 is an implant serving to replace a section of the aorta or an artery, the volume of which may be altered by means of a flexible substance incorporated into the walls of the vessel. This implant is intended to reduce pressure changes within the cardiovascular system.

WO 89/01765 A1 describes an implant and a method to increase the through-flow of blood by increasing arterial elasticity (arterial volume) and reducing pressure fluctuations (pulsation) in the arterial system, and to improve (increase) blood circulation in specific organs in order to counteract the damaging effects of cardiovascular illnesses.

EP 2 319 454 A1 discloses a compensatory container to affect blood pressure in accordance with the general term of Patent Claim 1 of the current application. Its key elements are an implant having a volume chamber with means to connect the volume chamber to a natural cardiovascular system, and with means of adjustment, with which a change in volume of a volume of the volume chamber can be enabled or effected with a change in pressure in the cardiovascular system or in the volume chamber. Such a change in volume is at most 10 $cm^3$ in a lower pressure region between 50 mmHg and a pressure threshold of at least 100 mmHg, and at least 10 $cm^3$ in an upper pressure region between the pressure threshold and 150 mmHg. The objective of the present invention is the further development of such a compensatory container.

This objective is achieved by means of the features of the current application.

Advantageous forms and further developments of the invention are the subject of the sub-claims.

The invention envisions that the means of adjustment comprise a frame and at least one flexible body acting in conjunction with this frame, with the frame and flexible body located outside the volume chamber and with the frame having two front parts and at least three support rods connecting the two front parts, with the at least one flexible body placed between them.

In other words, the compensatory container in accordance with the invention exhibits an internal volume chamber intended for the through-flow of blood, an external frame, and at least one flexible body acting in conjunction with this frame, with the frame and the flexible body functioning together as a means of adjustment and controlling the special pressure-dependent volume behavior of the volume chamber.

It is thus foreseen in accordance with the invention that the frame surrounding the volume chamber and having a flexible body should limit the change in volume of the volume chamber in a lower pressure region, while suddenly permitting or effecting a large change in volume above a particular pressure threshold, which may be preset. The flexible body fixed in the frame responds in a preferred embodiment in the manner of a buckling bar, which suddenly bends laterally only when a particular bending load is exceeded. In the compensatory container according to the invention, the flexible device exerts a corresponding pressure from outside on the volume chamber, so that, in a lower blood pressure region, only minimal changes in volume of the volume chamber are permitted. Above this pressure threshold level, however, the flexible body is unable to withstand the blood pressure exerted from inside on the wall of the volume chamber, and flexes suddenly outward. This abruptly increases the volume of the volume chamber, thereby lowering the blood pressure.

The special pressure-dependent behavior of the flexible body is determined among other things by the interaction of the flexible body with the frame, which acts as a thrust support, and which, in accordance with the invention, consists of two front parts and at least three support rods connecting the front parts. The flexible body is fixed in the stable frame formed by the front parts and the supporting rods in such a way that, depending on the blood pressure in the volume chamber, it can abruptly transition from a position restricting the change in volume of the volume chamber to a position allowing a significant change in volume of the volume chamber. Conversely, with sinking blood pressure in the region of the pressure threshold, the flexible body reverts to a position in which the change in volume of the volume chamber is restricted. The supporting rods and front parts are preferably to be made of stiff materials such as steel, titanium, or reinforced plastics.

The connection of the volume chamber to natural blood vessels, in particular in the vicinity of the aorta, is effected ideally by suturing in the area of the connective means in the conventional manner. Further fixing, if necessary also to nearby tissue, may be carried out with the aid of the frame, which can be provided for this purpose with holes or tabs in the area of the front parts through which suture material may be threaded. The compensatory container in accordance with the invention is fundamentally capable of installation in parallel, as in a bypass, or in line with a natural blood vessel.

The volume chamber is preferably manufactured as a woven or textile tube made of polyester. Polyester fabric has high tensile strength and lateral flexibility, and has proven its worth in aortic implants. Alternatively, other materials suitable for aortic implantation may be used. The volume chamber through which blood flows undergoes a change in shape depending on the blood pressure conditions; it is able to replicate the natural "windkessel function". The windkessel function is the retention in the elastic arteries of a portion of the volume of blood ejected by the heart during the systole and its continual release during the diastole, thus smoothing out the blood flow. These minimal changes in volume of the volume chamber in a lower pressure region that determine the air vessel effect, and which are intended to replicate those of natural blood vessels, are enabled by the means of adjustment in accordance with the invention, while large changes in volume of the volume chamber are only effected when a critical pressure threshold is exceeded.

In accordance with one embodiment of the invention, the front parts have sockets for receiving the support rods, in which the support rods are inserted in such a way as to resist torsion.

A further suggestion envisions that the flexible body should have openings for the support rods, with the openings ideally also being connected to the support rods in a torsion-resistant manner. The torsion-resistant connection of the support rods with the sockets and especially of the support rods with the openings in the flexible body prevents the material of the flexible body, the support rods, and the sockets from being overstressed through permanent torsional force and associated friction, which would place them at risk of rapid wearing. The torsion-resistant mounting also ensures that, as blood pressure gradually increases in the volume chamber, the flexible body does not gradually flex outward in consequence of a slight twisting relative to the support rods. Rather, in accordance with this embodiment of the invention, the position of the flexible body with respect to the support rods is entirely fixed in the area of the openings, thus increasing the effect of the abrupt transition of the flexible body from the volume-restricting to the volume-releasing position. At the same time, this permits the triggering of the return motion at a relatively high pressure.

It has been shown that a planar flexible body made of silicon exhibits the desired flexing response. Alternatively, the flexible body may be made of, e.g., polyurethane. Through the use of varying dimensions, material thicknesses, and/or material profiles, the desired flexing behavior, i.e. specifically the pressure threshold and the increase in volume in the upper pressure region, can be determined in advance and adjusted to meet the individual needs of a patient to be treated.

In accordance with one embodiment of the invention, the flexible body is located at least in part adjacent to the exterior wall of the volume chamber. Through this direct contact with the volume chamber, the pressure on the wall of the volume chamber exerted by the blood pressure is transmitted directly to the flexible body.

In a preferred embodiment of the invention, the frame has four support rods connecting the two front parts, and the flexible body four flexible surfaces, with each flexible surface situated between two adjoining support rods. The frame thus takes on a cuboid form, with the four support rods forming the edges of the cube and the four flexible wall surfaces its lateral faces.

A further suggestion envisions, in the lower pressure region, two flexible surfaces of the flexible body facing one another and having a concave curvature, with the two other flexible surfaces having a convex curvature, while in the upper pressure region, all four flexible surfaces of the flexible body should have a convex curvature. The primary flexing effect of the flexible body is thus generated by the two flexible surfaces having a concave curvature, i.e. curved toward the volume chamber, in the lower pressure region; these surfaces abruptly alter their curvature above the pressure threshold and spring outward. Through the concave curvature of two flexible surfaces in the lower pressure region, the elastic volume chamber can be shaped into a bone shape. Only once blood pressure rises above the pressure threshold is the pressure on the wall of the volume chamber, and thus on the flexible surfaces adjacent to it, great enough that these surfaces abruptly flex outward, expanding the bone-shaped cross-section of the volume chamber to a circular or elliptical cross-section. The increase in volume of the volume chamber associated with this expansion leads to the desired decrease in blood pressure.

The relation of length to width to height of a compensatory container in accordance with the invention is typically around 1:0.4:0.5. Thus, for example, with a compensatory container having a length of 90 mm to 130 mm, the preferred width would be in a range between 36 mm and 53 mm and the height in a range between 45 mm and 65 mm.

Figure 2:
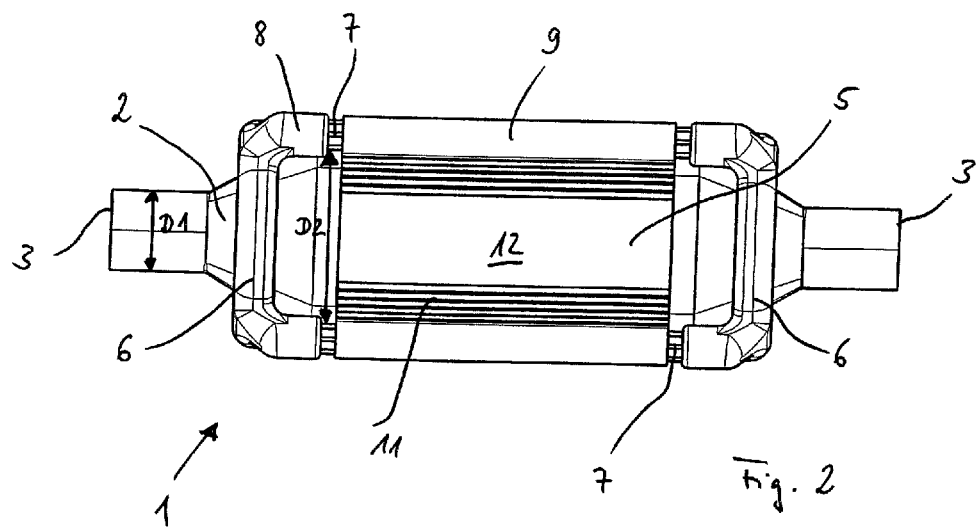
Figure 3:
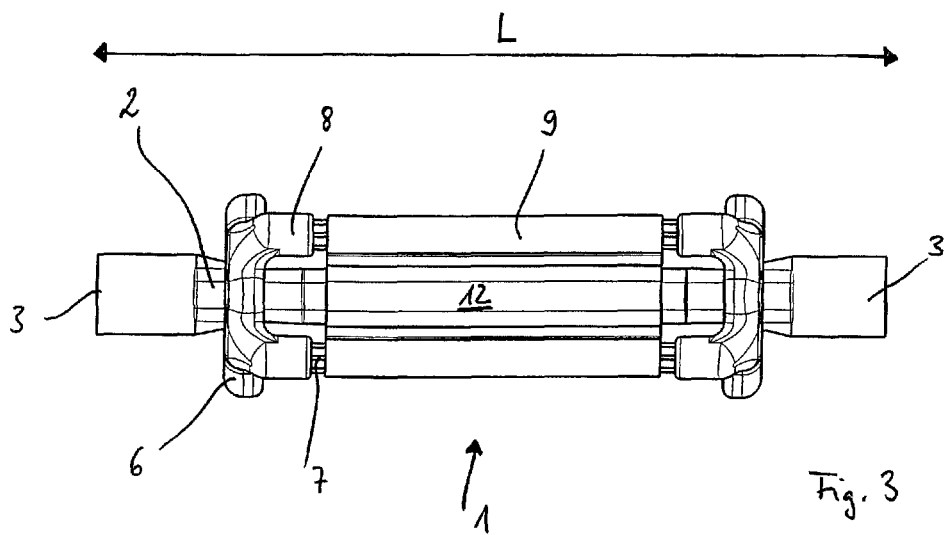
Figure 4:
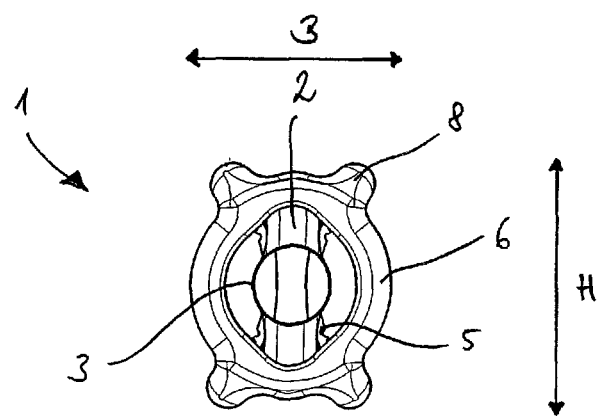

The invention is described hereinafter in greater detail by means of an example embodiment and with reference made to the attached illustrations. Shown are:

FIG. 1 a compensatory container in accordance with the invention, in perspective view;

FIG. 2 a compensatory container in accordance with the invention, in lateral view;

FIG. 3 a compensatory container in accordance with the invention, in top view;

FIG. 4 a compensatory container in accordance with the invention, viewed from above and the front.

FIGS. 1 through 4 depict a compensatory container in accordance with the invention, collectively numbered 1, in a state prior to connection to a natural blood vessel. It consists of an internally located, elongated volume chamber 2 made of polyester fabric, and frame 4 located outside volume chamber 2. Volume chamber 2 has at both ends connectors 3 for connecting to a natural blood vessel, with volume chamber 2 generally being sutured to the natural blood vessel near connectors 3. Connectors 3 have diameter D1, while volume chamber 2 gradually widens to diameter D2 in the transitional areas connecting to connectors 3; see FIG. 2. The actual values for diameters D1 and D2 depend, among other factors, on whether the compensatory container is installed in parallel, in the manner of a bypass, or in series with a natural blood vessel. In the bypass configuration, in which only a portion of the total blood volume flows through compensatory container 1, diameter D1 for example has a range of between 5 mm and 20 mm, ideally between 10 mm and 15 mm. If, by contrast, compensatory container 1 is installed in series, connectors 3 chosen and potentially volume chamber 2 itself must be of a larger size. In this case, diameter D1 is typically in the range of 20 mm to 40 mm, ideally between 25 mm and 35 mm.

Frame 4 surrounding volume chamber 2 consists of two front parts 6 of generally oval or annular shape and four support rods 7 connecting two front parts 6, whereby frame 4 may be somewhat shorter in length than volume chamber 2.

Volume chamber 2 is inserted into frame 4 in such a manner that two front parts 6 come to rest in the transitional areas described above in connection with the diameter increase of volume chamber 2, and connectors 3 project out of frame 4 through central openings in front parts 6; see FIGS. 1 and 2. Front parts 6 may also be designed with holes or tabs not depicted in the illustrations, such holes or tabs offering options in addition to connectors 3 for affixing compensatory container 1 to a natural blood vessel or nearby connective tissue.

Each of two front parts 6 has four attached sockets 8 for receiving support rods 7. As may be seen in particular from FIG. 4, sockets 8 are situated symmetrically, but in such a way that, in accordance with depiction in FIG. 4, the two upper sockets, and the two lower sockets are each slightly farther apart from one another than the left upper and left lower socket and the right upper and right lower socket. This configuration gives compensatory container 1 a relatively flat profile, which simplifies its insertion and positioning within a human body.

Frame 4 is completely erected with the aid of four support rods 7 inserted in sockets 8 of two front parts 6. Support rods 7 have a profile meshing with a corresponding inner profile of sockets 8, so that support rods 7 are installed in sockets 8 in such a way as to prevent torsion.

Between support rods 7 is installed one-piece flexible body 5 made of silicon. Flexible body 5 consists of four flexible surfaces 12 and four openings 9 for support rods 7. Analogously to sockets 8, openings 9 also have an internal profile meshing with inserted support rods 7 in such a manner that openings 9 and support rods 7 are connected with one another in such a way as to resist torsion.

The length of four flexible surfaces 12 fundamentally corresponds to the distance between two front parts 6 determined by the length of support rods 7, with the width of flexible surfaces 12 being in each case somewhat greater than the direct distance between two support rods 7 between which the corresponding flexible surface is placed. For this reason, flexible surfaces 12 between support rods 7 are not tightly spanned, but exhibit a degree of curvature. Two opposing flexible surfaces 12—in the depiction of FIG. 1, the right and the not visible left flexible surface 12—have a concave inward curvature, while the two remaining flexible surfaces 12—in accordance with FIG. 1, the upper and the also not visible flexible surface 12—have a convex outward curvature. Two flexible surfaces 12 having a concave curvature shall hereinafter be referred to as primary surfaces, and two flexible surfaces 12 having a convex curvature as secondary surfaces.

Both the primary and the secondary surfaces are situated against the exterior wall of volume chamber 2, and shape the cross-section of volume chamber 2 in such a way that it takes on a bone-shaped form, as indicated in FIG. 4. The spring forces of the secondary surfaces may be very small in comparison with those of the primary surfaces. Important functions of the secondary surfaces are the guidance and fixing of the volume chamber and the targeted disruption or reshaping of the pressure arc generated by the primary surfaces under conditions of high blood pressure in order to trigger the sudden outward flexing of the primary surfaces.

The exemplary embodiment of compensatory container 1 illustrated in the figures has a length L of 112 mm, a width W of 43 mm, and a height H of 52 mm; see FIGS. 3 and 4.

If compensatory container 1 in accordance with the invention is then connected with the natural blood vessel in the manner described above, it exhibits behavior that varies depending on the prevailing blood pressure. In a lower pressure region below a pressure threshold of 100 mmHg, compensatory container 1 behaves essentially as a natural blood vessel. It is thus able to replicate the air vessel effect described above and so permits small changes in volume of volume chamber 2; however, these are limited to a maximum of 10 $cm^3$ by flexible body 5 acting in conjunction with frame 4 and adjoining volume chamber 2 from the outside.

If, however, the blood pressure exceeds the pressure threshold, the pressure on the wall of volume chamber 2 and thus on flexible surfaces 12 adjacent to volume chamber 2 is so great that the two primary surfaces having concave curvatures abruptly flex outward and shift to a state in which they exhibit convex curvatures. The cross-section of volume chamber 2 accordingly changes suddenly from the bone shape of the lower pressure region to a more circular or elliptical shape; flexible body 5 in the vicinity of support rods 7 does not twist, in consequence of the torsion-resistant connection between flexible body 5 and support rods 7. With the change in cross-section, the volume of volume chamber 2 abruptly increases by an additional approximately 20 $cm^3$, thus decreasing blood pressure. Peak blood pressures of, for example, some 150 mmHg may in this manner be attenuated to approximately 115 mmHg. The total change in volume of the volume chamber 2 is 20 to 40 $cm^3$, ideally approximately 30 $cm^3$.

This ensures that, in pressure regions corresponding to normal blood pressure levels, compensatory container 1 has no effect exceeding that of the natural air vessel effect, while high blood pressure can be effectively lowered. Compensatory container 1 is ideally used to treat persons with chronic high blood pressure, in whom the compensatory container 1 functions permanently in the manner described above. However, due to its adaptability to different blood pressure levels, it is fundamentally also suitable to be implanted in persons suffering only from situationally elevated blood pressure, with blood pressure values otherwise at normal levels. This flexibility represents a significant advantage of the compensatory container in accordance with the invention as compared with drug therapy.

Torsion-resistant connection of support rods 7 with sockets 8 of front parts 6, and in particular with openings 9 of flexible body 5, support the effect of the abrupt expansion of volume chamber 2. The torsion-resistant connection prevents flexible surfaces 12 from flexing outward in consequence of the twisting of openings 9 in relation to support rods 7 as pressure in volume chamber 2 increases and thus gradually responding to the changed pressure levels. Rather, flexible surfaces 12 are firmly attached under tension on their long sides in the frame, which functions as a thrust support, and flexible surfaces 12 can only flex abruptly when the pressure threshold is exceeded. Seen in cross-section, the primary surfaces thus exhibit similar behavior to a buckling bar under tension. When, as a result, the blood pressure again drops below the pressure threshold, the primary surfaces spring back to their original position.

Support rods 7 are ideally designed to be resistant to torsion and lateral flexing. Such elasticity as still possessed by supporting rods 7 affects the flexing behavior of flexible body 5.

The specific flexing behavior of the primary surfaces and thus of the pressure threshold may be determined e.g. by means of the thickness of flexible surfaces 12 and/or ridged profile 11 of the primary surfaces, thereby making the flexible surfaces more or less elastic. The secondary surfaces with convex curvatures and the specific dimensions of the primary and secondary surfaces also have an effect on the transition behavior of the primary surfaces.

By means of the compensatory container in accordance with the invention, blood pressure may be effectively lowered, and this generally without the need for additional medication.

The invention claimed is:

1. A compensatory container to affect blood pressure, comprising volume chamber with connectors to connect volume chamber to a natural cardiovascular system, in which a pressure change in the cardiovascular system can effect a change in volume of volume chamber, further comprising means of adjustment, which limit the change in volume of volume chamber in a lower pressure region below a pressure threshold of at least 100 mmHg to a maximum of 10 cm$^3$, and which effect a change in the volume of volume chamber in an upper pressure range between the pressure threshold and 150 mmHg of at least of 10 cm$^3$, wherein the means of adjustment comprise frame and at least one flexible body acting in conjunction with this frame, with frame and flexible body located outside volume chamber, and with frame having two front parts and at least three support rods connecting two front parts, with the at least one flexible body placed between them.

2. Compensatory container in accordance with claim 1, wherein front parts have sockets for receiving support rods, and in which support rods are installed in such a manner as to resist torsion.

3. Compensatory container in accordance with claim 1, wherein flexible body has openings for support rods.

4. Compensatory container in accordance with claim 3, wherein openings are connected with support rods in such a manner as to resist torsion.

5. Compensatory container in accordance with claim 1, wherein flexible body is made of silicon.

6. Compensatory container in accordance with claim 1, wherein flexible body is situated at least in part adjacent to exterior wall of volume chamber.

7. Compensatory container in accordance with claim 1, wherein flexible body has profiled surface.

8. Compensatory container in accordance with claim 1, wherein volume chamber is made of polyester.

9. Compensatory container in accordance with claim 1, wherein frame has four support rods connecting two front parts.

10. Compensatory container in accordance with claim 1, wherein flexible body encompasses flexible surfaces, whereby one flexible body is situated between every two adjoining support rods.

11. Compensatory container in accordance with claim 10, wherein, in the lower pressure region, at least one flexible surface of flexible body has a concave curvature and at least one flexible surface of flexible body has a convex curvature, while, in the upper pressure region, all flexible surfaces of flexible body have a convex curvature.

12. Compensatory container in accordance with claim 11, wherein flexible body encompasses four flexible surfaces, with, in the lower pressure region, two flexible surfaces of flexible body facing one another and having a concave curvature and the two other flexible surfaces having a concave curvature, while, in the upper pressure region, all four flexible surfaces of flexible body have a convex curvature.

* * * * *